(12) United States Patent
Divita et al.

(10) Patent No.: US 7,514,530 B2
(45) Date of Patent: Apr. 7, 2009

(54) PEPTIDE CARRIER FOR DELIVERING SIRNA INTO MAMMALIAN CELLS

(75) Inventors: Gilles Divita, Mauguio (FR); May Catherine Morris, Mauguio (FR); Frédéric Heitz, Grabels (FR); Federica Simeoni, Montpellier (FR)

(73) Assignee: Centre National de la Recherche Scientifique, Paris (FR)

( * ) Notice: Subject to any disclaimer, the term of this patent is extended or adjusted under 35 U.S.C. 154(b) by 431 days.

(21) Appl. No.: 10/831,342

(22) Filed: Apr. 26, 2004

(65) Prior Publication Data

US 2005/0239687 A1  Oct. 27, 2005

(51) Int. Cl.
  *C07K 7/00* (2006.01)
  *C07H 21/04* (2006.01)
  *A61K 31/70* (2006.01)
(52) U.S. Cl. .................. 530/324; 536/24.5; 514/44
(58) Field of Classification Search .................. None
  See application file for complete search history.

(56) References Cited

U.S. PATENT DOCUMENTS

| 6,300,120 | B1 * | 10/2001 | Nakanishi et al. ...... 435/252.33 |
| 6,432,658 | B1 * | 8/2002 | Hoogendoorn et al. ........ 435/13 |
| 6,841,535 | B2 * | 1/2005 | Divita et al. ................. 530/324 |
| 2003/0125281 | A1 * | 7/2003 | Lewis et al. .................... 514/44 |
| 2003/0148519 | A1 * | 8/2003 | Engelke et al. .............. 435/455 |
| 2004/0147027 | A1 * | 7/2004 | Troy et al. ................... 435/458 |

OTHER PUBLICATIONS

Elbashir et al. Nature 2001, vol. 411, pp. 494-498.*
Morris et al. Nucleic Acids Research 1997, vol. 25, pp. 2730-2736.*
Federica Simeoni, et al. "Insight Into the Mechanism of the Peptide-based Gene Delivery System MPG: Implications for Delivery of siRNA into Mammalian Cells." *Nucleic Acids Research*. vol. 31, No. 11, pp. 2717-2724, Jun. 2003.

* cited by examiner

*Primary Examiner*—Tracy Vivlemore
(74) *Attorney, Agent, or Firm*—Morgan, Lewis & Bockius LLP (57) ABSTRACT

Complex comprising a peptide carrier of SEQ ID NO:1 GALFLGFLGAAGSTMGAWSQPKR$_1$KRKVR$_2$ and an appropriate siRNA, wherein $R_1$ represents any amino acid residue and more preferably K or S, $R_2$ is null or represents one of the following groups: cysteamide, cysteine, thiol, amide, linear or ramified $C_1$-$C_6$ alkyl optionally substituted, primary or secondary amine, osidic derivative, lipid, phospholipid or cholesterol and said siRNA is selected to silence a target mRNA.

7 Claims, 8 Drawing Sheets

Figure 6: MPG mediated delivery of Cyclin B1 inhibitors

MCF-7 cells were treated with MPG/siRNA or Oligofectamine/siRNA complexes and Cyclin B1 protein level was determined after 2 days.

Figure 7: Cyclin-B1 siRNA inhibits proliferation of cancer cells

MCF-7 cells were treated on day 1 with siRNA and MPG/siRNA complexes and cell proliferation was analyzed 7 days later.

SEQUENCE LISTING

```
<160> NUMBER OF SEQ ID NOS: 11

<210> SEQ ID NO 1
<211> LENGTH: 28
<212> TYPE: PRT
<213> ORGANISM: Artificial sequence
<220> FEATURE:
<223> OTHER INFORMATION: carrier peptide
<220> FEATURE:
<221> NAME/KEY: MISC_FEATURE
<222> LOCATION: (23)..(23)
<223> OTHER INFORMATION: Xaa= any amino acid residue
<220> FEATURE:
<221> NAME/KEY: MISC_FEATURE
<222> LOCATION: (28)..(28)
<223> OTHER INFORMATION: Xaa= null, a cysteamide group, a carboxyl group
      or an amide group

<400> SEQUENCE: 1

Gly Ala Leu Phe Leu Gly Phe Leu Gly Ala Ala Gly Ser Thr Met Gly
1               5                   10                  15

Ala Trp Ser Gln Pro Lys Xaa Lys Arg Lys Val Xaa
            20                  25

<210> SEQ ID NO 2
<211> LENGTH: 27
<212> TYPE: PRT
<213> ORGANISM: Artificial sequence
<220> FEATURE:
<223> OTHER INFORMATION: carrier peptide

<400> SEQUENCE: 2

Gly Ala Leu Phe Leu Gly Phe Leu Gly Ala Ala Gly Ser Thr Met Gly
1               5                   10                  15

Ala Trp Ser Gln Pro Lys Lys Lys Arg Lys Val
            20                  25

<210> SEQ ID NO 3
<211> LENGTH: 27
<212> TYPE: PRT
<213> ORGANISM: Artificial sequence
<220> FEATURE:
<223> OTHER INFORMATION: carrier peptide
```

-continued

```
<400> SEQUENCE: 3

Gly Ala Leu Phe Leu Gly Phe Leu Gly Ala Ala Gly Ser Thr Met Gly
1               5                   10                  15

Ala Trp Ser Gln Pro Lys Ser Lys Arg Lys Val
            20                  25

<210> SEQ ID NO 4
<211> LENGTH: 21
<212> TYPE: DNA
<213> ORGANISM: Artificial sequence
<220> FEATURE:
<223> OTHER INFORMATION: siRNA

<400> SEQUENCE: 4
cuuacgcuga guacuucgat t                                              21

<210> SEQ ID NO 5
<211> LENGTH: 21
<212> TYPE: DNA
<213> ORGANISM: Artificial sequence
<220> FEATURE:
<223> OTHER INFORMATION: siRNA

<400> SEQUENCE: 5
ttgaaugcga cucaugaagc u                                              21

<210> SEQ ID NO 6
<211> LENGTH: 21
<212> TYPE: DNA
<213> ORGANISM: Artificial sequence
<220> FEATURE:
<223> OTHER INFORMATION: siRNA

<400> SEQUENCE: 6
cguacgcgga auacuucgat t                                              21

<210> SEQ ID NO 7
<211> LENGTH: 21
<212> TYPE: DNA
<213> ORGANISM: Artificial sequence
<220> FEATURE:
<223> OTHER INFORMATION: siRNA

<400> SEQUENCE: 7
ttgcaugcgc cuuaugaagc u                                              21

<210> SEQ ID NO 8
<211> LENGTH: 21
<212> TYPE: DNA
<213> ORGANISM: Artificial sequence
<220> FEATURE:
<223> OTHER INFORMATION: siRNA

<400> SEQUENCE: 8
ggcgaagauc aacauggcat t                                              21

<210> SEQ ID NO 9
<211> LENGTH: 21
<212> TYPE: DNA
<213> ORGANISM: Artificial sequence
<220> FEATURE:
<223> OTHER INFORMATION: siRNA

<400> SEQUENCE: 9
ugccauguug aucuucgcct t                                              21
```

```
<210> SEQ ID NO 10
<211> LENGTH: 21
<212> TYPE: DNA
<213> ORGANISM: Artificial sequence
<220> FEATURE:
<223> OTHER INFORMATION: siRNA

<400> SEQUENCE: 10
ggugaagauc agcauggcat t                                                  21

<210> SEQ ID NO 11
<211> LENGTH: 21
<212> TYPE: DNA
<213> ORGANISM: Artificial sequence
<220> FEATURE:
<223> OTHER INFORMATION: siRNA

<400> SEQUENCE: 11
ugccaugucg aucuucacct t                                                  21
```

PEPTIDE CARRIER FOR DELIVERING SIRNA INTO MAMMALIAN CELLS

FIELD OF THE INVENTION

The present invention relates to methods and compositions for delivering siRNA into mammalian cells, said compositions being able to treat human and animal diseases. The present invention relates also to a specific peptide carrier (or transfecting peptide vector).

DESCRIPTION OF THE RELATED ART

The development of non-viral based gene delivery systems constitutes an essential challenge in therapeutics. Although they exhibit several advantages over viral systems, the interest of non-viral synthetic gene delivery systems for therapeutic applications remains limited by their poor ability to escape from the endosomal compartment and to translocate DNA into the nucleus (1). During the past ten years, several peptide-based gene delivery systems that can overcome both extracellular and intracellular limitations have been proposed (2, 3, 4). Poor release from the endosomal compartment after cellular uptake constitutes one of the major limitations of non-viral gene delivery systems. Research has therefore been focused on the design of strategies to either facilitate release from the endosome or to bypass the endosomal pathway (2, 3, 4). Peptide carriers that combine DNA binding and membrane-destabilizing properties have been demonstrated to promote gene transfer into cultured cells (5, 6) and living animals (7).

Another major limitation of non-viral gene delivery systems is the poor nuclear delivery of DNA, which is however essential for transfection of non-dividing cells as well as for in vivo applications. In order to improve nuclear delivery of DNA, synthetic peptides containing nuclear localization sequences (NLS) have been extensively used (8, 9). Protein transduction domains (PTD) cross the cell membrane independently of the endosomal pathway and have been used to improve the delivery of DNA (10, 11). The third helix of *Antennapedia* homeodomain has been shown to form stable non-covalent complexes with small oligonucleotides and to facilitate their internalization in a non-endosomal fashion (12). The NLS domain of Tat has been shown to promote nuclear targeting of proteins and DNA (10, 11, 13). Tat peptide covalently attached to liposomes promotes rapid delivery of DNA, independently of the endosomal pathway (14, 15). In contrast, oligomers of the arginine-rich motif of HIV-1 Tat protein have been reported to form stable particles with DNA through non-covalent interactions, but promote their delivery into cells through the endosomal pathway (16).

A new peptide-based gene delivery system, MPG, which forms stable non-covalent complexes with nucleic acids and promotes their delivery into a large panel of cell lines has recently been described (17, 18, 19).

MPG is a bipartite amphipathic peptide derived from both the fusion peptide domain of HIV-1 gp41 protein and the nuclear localization sequence of SV40 large T antigen.

More specifically:

Morris M C et al. (17) have shown that this peptide vector exhibits high affinity for single- and double-stranded oligonucleotides (DNA) and is able to deliver them into mammalian cells in <1 h, independently of the endosome pathway. However, they have also shown that the affinity of MPG for single-stranded oligonucleotides was at least 2-fold higher than for double-stranded oligonucleotides.

Morris M C et al. (18) have also shown that this peptide vector exhibits high affinity for nucleic acids and protect them from degradation; they have therefore demonstrated that the use of MPG as an efficient agent for the delivery of short oligonucleotides can be generalized to the efficient delivery of plasmid expression vectors and full-length antisense cDNA. MPG not only presents high affinity for nucleic acids, but also protects them against nucleases. They have observed a rapid self-assembly between MPG and DNA, which involves electrostatic interactions, as already proposed for cationic peptides and then promotes further peptide-peptide interactions, leading to the formation of a protective "cage" around the DNA molecule.

Vidal P et al (19) have shown that the same peptide MPG may also be used for RNA cell delivery and more specifically for the cell delivery of large fragments of mRNA.

Pursuing their work, some of the Authors of the here above cited publications, have now confirmed that the mechanism through which MPG promotes gene delivery into cells is independent of the endosomal pathway. They have also now shown that the nuclear localization sequence (NLS) of MPG is required for both electrostatic interactions with DNA and nuclear targeting, and that MPG/DNA particles interact with the nuclear import machinery.

Moreover they have now unexpectedly shown that said MPG peptide and a variant characterized by a mutation in the NLS may deliver siRNA into mammalian cells.

RNA interference (siRNA) constitutes a powerful tool to silence gene expression post-transcriptionally (28, 29); however, it does not exist until now efficient non-viral based delivery systems of siRNA in vivo (i.e. as a drug). Indeed, delivery of siRNA to a subcellular target requires a rapid release of siRNA into the cytoplasm for significantly improving the silencing response.

The inventors have now found that, unexpectedly, MPG and peptides derived from MPG are capable of efficiently transfecting siRNA (i.e. double-strand small RNA molecules), either in the nucleus or in the cytoplasm of the target cell, in the absence of liposomes or specific treatment of the concerned cells.

Therefore in a first aspect, the subject-matter of the present invention is a complex comprising a peptide carrier of SEQ ID NO:1 GALFLGFLGAAGSTMGAWSQPKR$_1$KRKVR$_2$ and an appropriate siRNA, wherein R$_1$ represents any amino acid residue and more preferably K or S, R$_2$ is null or represents one of the following groups: cysteamide, cysteine, thiol, amide, linear or ramified C$_1$-C$_6$ alkyl optionally substituted, primary or secondary amine, osidic derivative, lipid, phospholipid or cholesterol and said siRNA is selected to silence a target mRNA.

In accordance with the invention, in the case where R$_1$=K, the peptide carrier is MPG (SEQ ID NO:2) and in the case where R$_1$=S, the peptide carrier is MPG$^{\Delta NLS}$ (SEQ ID NO:3).

According to an advantageous embodiment of said complex, said peptide carrier and said siRNA are preferentially in a ratio of 1:1 to 20:1 (molar ratio), preferably in a ratio of 10:1.

Unexpectedly, delivery of siRNA by both MPG and its NLS mutant enable robust downregulation of target mRNA. Nevertheless, the NLS mutant induces rapid release of the siRNA into the cytoplasm, and this correlates with a more significant biological response. Taken together, these results support the potential of MPG for therapeutic applications.

Therefore, peptide carriers of SEQ ID NO: 1 are enable to deliver siRNA into cultured cells with high efficiency. Indeed, in all cases, the selected siRNA, combined with said peptide carrier, penetrates into the cell (internalization) and keeps its biological properties. Moreover, the siRNA delivery by means of said complexes is independent of the presence of serum.

In a second aspect, the subject-matter of the present invention is the peptide carrier of SEQ ID NO:2. Unexpectedly said peptide carrier may be used to deliver both DNA and RNA of small size in the cytoplasm of the target cell, with high efficiency.

In a third aspect, the subject-matter of the present invention is a composition which comprises a complex as defined above and a suitable vehicle.

The complexes and compositions according to the invention have many applications as medicaments, in human and veterinary medicine:
  in human and animal gene therapy, in particular in hereditary diseases
  as antiviral agents
  as anticancer agents
  as inhibitors in conditions where there is an overexpression of a biological substance, leading to a pathological state.
  They may be administered ex vivo or in vivo.

In another aspect, the subject-matter of the invention is also a transfection kit comprising at least appropriate buffers, positive and negative controls and at least a complex as defined above, said complex being either in solution or lyophilized.

In another aspect, the subject-matter of the invention is a method of preventing or treating a disease of a mammal, wherein at least one symptom of the disease is mediated at least in part by the presence of abnormal mRNA in the mammal to be treated, wherein the method comprises administering to the mammal an amount of a complex as defined above sufficient to silence said abnormal mRNA to thereby prevent or treat the corresponding disease.

In another aspect, the subject-matter of the invention is a method of delivering a siRNA to a target cell, said method comprising:
  providing a complex according to the invention and
  contacting a target cell with said complex.

According to said methods, said complex comprises a molar ratio of peptide carrier:siRNA of at least 1:1 to 20:1, (molar ratio), preferably in a ratio of 10:1.

In addition to the preceding features, the invention also comprises other features which will emerge from the description which follows, which refers to exemplary embodiments of the invention as well as to the accompanying drawings in which:

FIG. 1: MPG-mediated gene delivery in the presence of inhibitors of the endosomal pathway. A/MPG/DNA complexes formed at a charge ratio of 5/1 with 100 ng pRL-SV40 plasmid encoding the reporter gene luciferase were overlaid onto human fibroblasts (Hs68) in the presence of either bafilomycin A (Baf-A: 150 nM), cytochalasin B (Cy-B: 50 µg/ml) or chloroquine (Chl: 100 µM). After 48 hrs cell extracts were prepared and luciferase activity was measured and reported as a function of total protein (black). Similar experiments were performed using a lipid-based delivery system, Lipofectamine™, as a control (white). Experiments in the absence of inhibitors were also performed using an MPG peptide lacking a C-terminal cysteamide group (grey). B/A 36mer fluorescein labelled oligonucleotide was complexed with MPG at a charge ratio of 5/1. Complexes were then overlaid onto cultured Hela cells in the presence of bafilomycin A (middle panel) or cytochalasin B (bottom panel) and cellular localization of the oligonucleotide was monitored by fluorescence microscopy on living cells 1 hr after transfection. A control experiment with free oligonucleotide is shown in the top panel.

FIG. 2: The NLS of MPG is essential for nuclear translocation: A/Purified GST-importin $\alpha$ and $\beta$ were coupled onto GST Sepharose resin and incubated in batch with MPG/DNA or MPG$^{\Delta NLS}$/DNA complexes for 1 hr, extensively washed and incubated with 50 nM glutathione to elute the complexes. DNA was then extracted and analyzed by agarose gel electrophoresis (0.8%). Lane 1: control DNA; lane 2: free plasmid does not associate with importin $\alpha$; lane 3: binding of MPG/DNA to importin $\alpha$; lane 4: binding of MPG/DNA to importin $\beta$; lane 5: MPG/DNA does not associate with importin $\beta$. B/Delivery of pRL-SV40 plasmid: MPG/DNA (black boxes) or MPG$^{\Delta NLS}$/DNA (grey boxes) complexes formed at a charge ratio of 5/1 with 100 ng pRL-SV40 plasmid encoding the reporter gene luciferase were overlaid onto synchronized or arrested (-FCS) human fibroblasts (Hs68). Luciferase activity was monitored 12 hrs and 24 hrs after release from synchrony, or after 24 hrs for arrested cells and 48 hrs for asynchronous cells. Control transfections were performed with Lipofectamine™ (white boxes) or naked plasmid (dashed boxes).

FIG. 4: MPG-mediated delivery of siRNA induces a robust biological response. A/MPG mediated delivery of siRNA targeting luciferase gene. MPG/siRNA or MPG$^{\Delta NLS}$/DNA complexes were formed in DMEM at a charge ratio 10:1 and incubated for 30 min at 37° C., then overlaid onto Cos-7 or HeLa cells grown to 60% confluence and previously transfected with the pRL-SV40 plasmid (Promega) encoding the reporter gene luciferase under control of an SV40 promoter. After 30 min incubation at 37° C., 1 ml of fresh DMEM supplemented with 10% fetal calf serum was added onto the cells. Luciferase activity was measured 48 hrs after transfection. Transfections were also performed with Oligofectamine™ as a standard. Control experiments were performed with either naked siRNA or using a mismatch siRNA (dashed bars). B/MPG-mediated delivery of siRNA targeting GAPDH gene: Western blot analysis. Different concentrations of siRNA (25, 50, 100 nM) were transfected with either MPG or MPG$^{\Delta NLS}$ and the levels of GAPDH protein were analyzed by Western blotting 30 hrs post transfection. Actin was used as a control to normalize protein loading. C/MPG-mediated delivery of siRNA targeting GAPDH gene: Northern blot analysis. The kinetics of siRNA (50 nM)-induced degradation of GAPDH mRNA following transfection with either MPG or MPG$^{\Delta NLS}$ were analyzed by Northern blotting. Actin was used as a control to normalize mRNA levels in each sample.

EXAMPLE 1

Peptide Synthesis and Analysis

All peptides were synthesized by solid phase peptide synthesis using AEDI-expansin resin with a 9050 Pep Synthesizer (Millipore, Wartford, UK) according to Fmoc/tBoc method and purified as described previously (18). MPG and MPG$^{\Delta NLS}$ were acetylated at their N-terminus and synthesized with a cysteamide group at their C-terminus.

```
MPG:       GALFLGFLGAAGSTMGAWSQPKKKRKV    (SEQ ID NO:2)
and
MPG^ANLS   GALFLGFLGAAGSTMGAWSQPKSKRXV.   (SEQ ID NO:3)
```

Attachment of a cysteamide group to the C-terminus of MPG is performed according to the protocol described in Mery J. et al. (39).

Protocols of preparation and purification of peptides are the ones that are reported in Morris M C et al. (17).

EXAMPLE 2

MPG-Mediated siRNA Targeting Luciferase Delivery

1. Material and Methods

Cell Culture and MPG-Mediated Transfection.

Hs68 (ATCC n°CRL-1635), Cos-7 (ATCC n°CRL-1651) and HeLa (ATCC n°CCL-2) cell lines were cultured in Dulbecco's Modified Eagle's Medium supplemented with 2 mM glutamine, 1% antibiotics (streptomycin 10 000 µg/ml, penicillin, 10'000 IU/ml) and 10% (w/v) fetal calf serum (FCS) at 37° C. in a humidified atmosphere containing 5% $CO_2$ as described previously (18). For MPG or MPG$^{\Delta NLS}$-mediated gene delivery, peptide carrier/siRNA complexes were formed in DMEM or PBS, at a charge ratio 10:1 and incubated for 30 min at 37° C. Cells grown to 60% confluence were then overlaid with these preformed complexes. After 30 min incubation at 37° C., 1 ml of fresh DMEM supplemented with 10% fetal calf serum was added to the cells, without removing the overlay of carrier/siRNA, and cells were returned to the incubator.

Transfections were performed for 1 hour, after which cells were extensively washed and either analyzed by fluorescence microscopy in order to determine the cellular localization of the fluorescently labeled oligonucleotide or returned to the incubator at 37° C. in the presence of fresh medium supplemented with serum.

MPG-Mediated siRNA Delivery.

siRNA targeting the 3'UTR of GAPDH were from the Silencer™ GAPDH siRNA kit (Ambion). Fluorescent labeling of siRNA was performed using either the Fam or the Cy3 Silencer™ labeling kit (Ambion) and modified as described in the manufacturer's protocol. pRL-Luc reporter gene was from Promega and siRNA targeting luciferase sense 5'CUUACGCUGAGUACUUCGATT3' (SEQ ID NO:4) and antisense 3'TTGAAUGCGACUCAUGAAGCU5' (SEQ ID NO:5) and mismatch sense 5'CGUACGCGGAAUACUUC-GATT3' (SEQ ID NO:6) and antisense 3'TTGCAUGCGCCU-UAUGAAGCU5' (SEQ ID NO:7) siRNA were obtained from Genset Oligos.

Northern Blotting.

Hs68 or HeLa cells ($5\times10^6$ cells) incubated with complexes were collected and total RNAs were isolated from cells using TriReagent™ (Sigma, Saint Louis) according to the manufacturer's recommendations. RNAs were then purified by phenol extraction followed by ethanol precipitation. RNA samples (10 µg) were separated by electrophoresis in formaldehyde agarose gels (1.2%), transferred onto nylon membranes (Hybond N+, Amersham Pharmacia Biotech) and hybridized with $^{32}$P-labelled GAPDH and actin probes (the latter used to normalize RNA loading). Signals were detected by Phosphorimaging (Molecular Dynamics) and quantified using ImageQuant software.

2. Results

Figure 3:
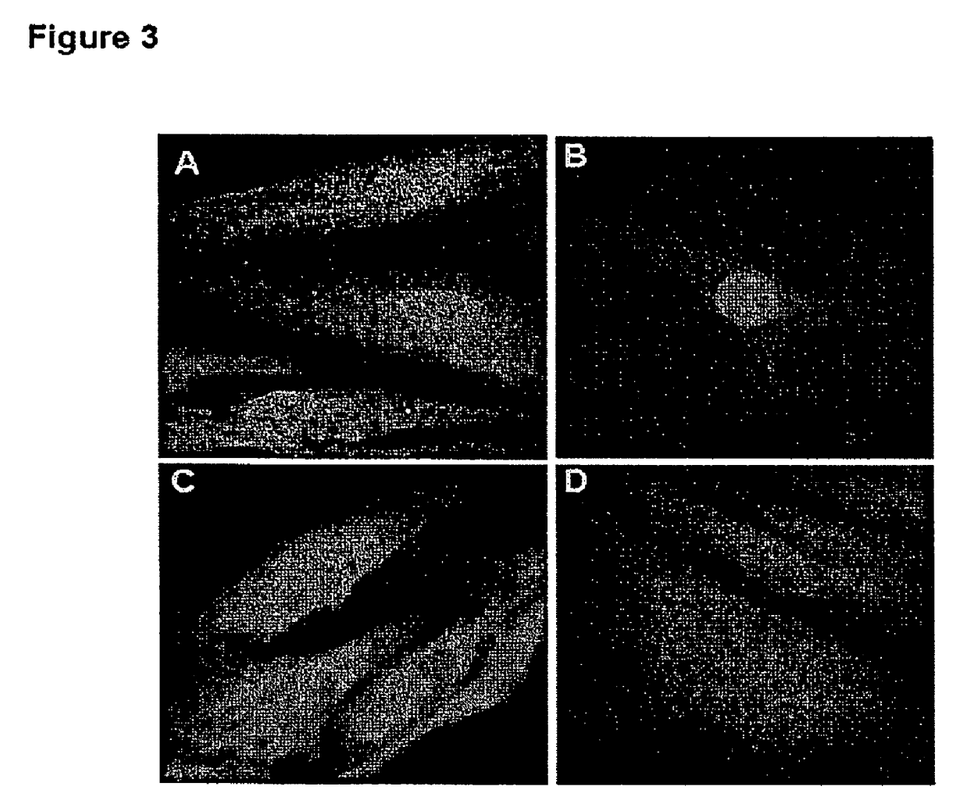
FIG. 3: MPG-mediated delivery of siRNA. siRNA designed to target GAPDH were fluorescently labeled using the Silence™ kits with fluorescein or Cy-3. siRNA/MPG (A, B) and siRNA/MPG$^{\Delta NLS}$ (C, D) complexes were overlaid onto cultured Hs68 and cellular localization of the siRNA was monitored by fluorescence microscopy on living cells 1 hr after transfection.

RNA interference (siRNA) constitutes a powerful tool to silence gene expression post-transcriptionally (28, 29). In order to validate the potential of MPG-like carriers, the ability of MPG and MPG$^{\Delta NLS}$ to promote cellular uptake of siRNA was investigated. Fluorescently-labelled siRNA designed to silence GAPDH were complexed with both MPG and MPG$^{\Delta NLS}$ at a molar ratio of 10/1, incubated onto cultured Hs68 human fibroblasts in the presence of serum for 30 min, following which internalization and subcellular localization of siRNA were examined by fluorescence microscopy. Two different fluorescent probes (fluorescein and Cy-3), were used in order to avoid any artefacts which might have been associated with the nature of the probe. As fixation procedures have sometimes been reported to cause artifactual uptake (30-32), experiments were performed on living cells. As shown in FIG. 3, both peptide carriers were able to deliver siRNA into cultured cells with high efficiency (about 90% cells). Interestingly, the final subcellular localization of the siRNA was dependent on the MPG carrier used. Fluorescently-labeled siRNA localized rapidly to the nucleus when transfected with MPG, but remained mostly in the cytoplasm when transfected with MPG$^{\Delta NLS}$. Moreover, these experiments demonstrate that MPG-mediated siRNA delivery is independent of the presence of serum.

Figure 4:
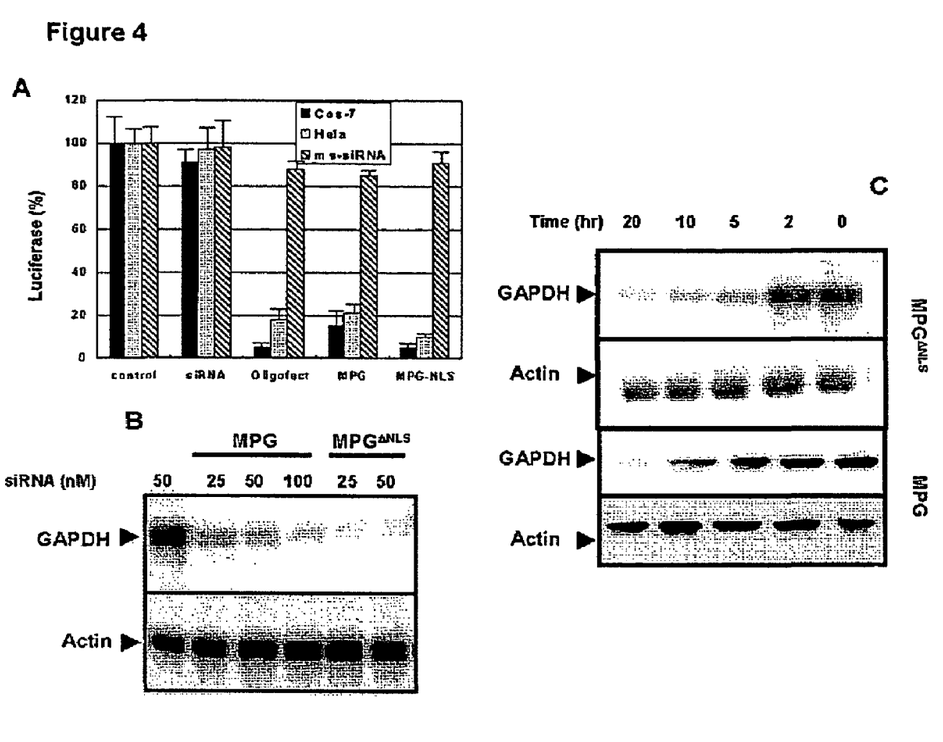

The biological response of MPG-mediated siRNA delivery was next investigated. Two series of experiments were performed. First the protocol described by Elbashir et al. (28) was used: Hela and Cos-7 cells transfected with the plasmid encoding the reporter gene luciferase were incubated with siRNA/MPG or siRNA/MPG$^{\Delta NLS}$ complexes in which the siRNA was designed to silence luciferase and luciferase activity was measured 48 hrs later. 50 nM siRNA was associated with either MPG or MPG$^{\Delta NLS}$ at a charge ratio of 10/1. As a control, siRNA transfection was performed with the commercially available lipid-based delivery system Oligofectamine™. MPG-mediated delivery of siRNA yielded a decrease of 78% and 85% of luciferase activity in Cos-7 and HeLa cells, respectively (FIG. 4A). This effect was further enhanced to 90% and 95% by MPG$^{\Delta NLS}$. Similar experiments performed with a mismatch siRNA complexed with MPG or MPG$^{\Delta NLS}$ did not result in any change in levels of luciferase activity, suggesting that there is no side effect associated with the presence of MPG. These experiments revealed that the efficiency of MPG-like peptides is similar to that of Oligofectamine™, suggesting that MPG is able to release the siRNA rapidly and does not affect its biological effect upon cellular internalization.

EXAMPLE 3

MPG-Mediated Gene Delivery is Independent of the Endosomal Pathway

1. Material and Methods
Cell Culture and MPG-Mediated Transfection.
Hs68, Cos-7 and HeLa cell lines were cultured in Dulbecco's Modified Eagle's Medium supplemented with 2 mM glutamine, 1% antibiotics (streptomycin 10 000 µg/ml, penicillin, 10'000 IU/ml) and 10% (w/v) fetal calf serum (FCS) at 37° C. in a humidified atmosphere containing 5% $CO_2$ as described previously (18). For MPG or MPG$^{\Delta NLS}$-mediated gene delivery, peptide carrier/DNA complexes were formed in DMEM or PBS (500 µl of DMEM containing 100 ng of DNA complexed with MPG at a charge ratio 5:1) and incubated for 30 min at 37° C. Cells grown to 60% confluence were then overlaid with these preformed complexes. After 30 min incubation at 37° C., 1 ml of fresh DMEM supplemented with 10% fetal calf serum was added to the cells, without removing the overlay of carrier/DNA, and cells were returned to the incubator.

For cell cycle-dependent studies, Hs68 fibroblasts were synchronized by serum deprivation for 40 hrs, then restimulated to enter the cycle and grow into early G1 for 4 hrs by addition of fresh DMEM supplemented with 20% FCS, and incubated in the presence of MPG/DNA complexes as described above. Luciferase activity was monitored as described previously (19) and control transfection experiments were performed using Lipofectamine™. When transfected at 4° C., cells were incubated for 1 hour at 4° C. prior to transfection, then incubated with MPG/DNA complexes for another 2 hours at 4° C., extensively washed and finally returned to incubation at 37° C. in fresh medium supplemented with serum. When transfections were performed in the presence of bafilomycin A (175 nM), cytochalasin B (50 µg/ml) or chloroquine (100 µM), cells were preincubated with these inhibitors of endocytosis for 1 hour prior to transfection.

2. Results

Figure 1:
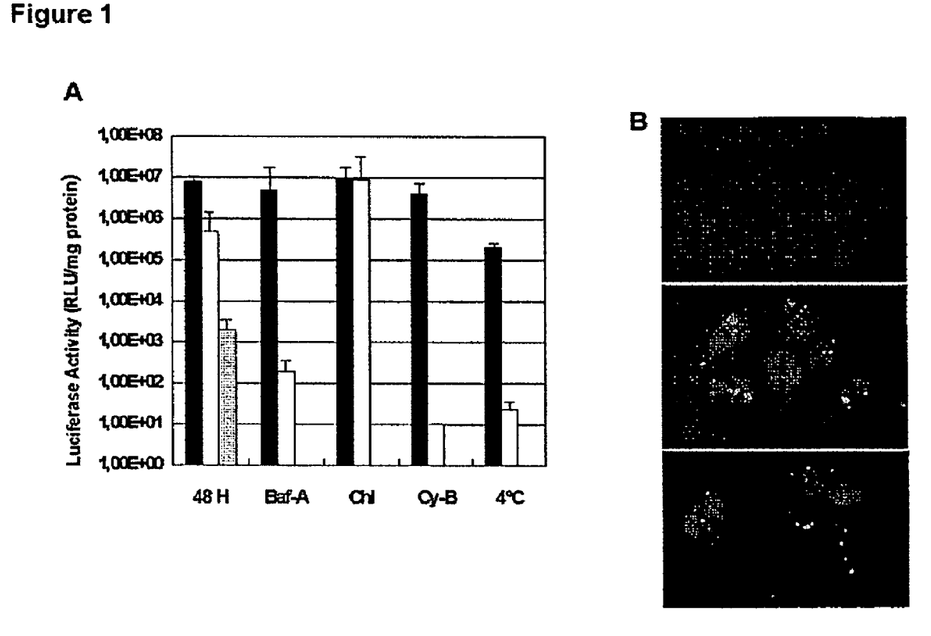

Transport of DNA into cells involves a number of selective steps, therefore understanding the mechanisms underlying each of these steps as well as the behavior of carrier/DNA complexes within the cell is essential to develop more efficient carriers. As specified here above, it was already reported that MPG can deliver oligonucleotides into mammalian cells at low temperature with high efficiency (17). In order to understand the mechanism through which MPG mediates gene delivery, transfection experiments were performed in the presence of several inhibitors that interfere with the endosomal pathway including cytochalasin B, bafilomycin A and chloroquine (FIG. 1). Cytochalasin B induces depolymerization of the microfilaments involved in phagocytosis and macro-pinocytosis without affecting other endocytotic processes (20). Bafilomycin A specifically prevents the acidification of early endosomes, by inhibiting a proton pump known as vacuolar ATPase (21) and chloroquine is a weak base, which inhibits the maturation of the transport vesicles into late endosomes and neutralizes the pH of the latter (22).

A plasmid encoding the reporter gene luciferase, pRL-SV40, was associated with MPG carrier at a charge ratio of 5:1 (MPG/DNA) and overlaid onto cultured human fibroblasts (Hs68) or HeLa cells in the presence of either bafilomycin A (150 nM), chloroquine (100 µM) or cytochalasin B (50 µg/ml). Transfection efficiency was monitored 30 hrs after transfection and Lipofectamine™ was used as a standard control method for transfection. As shown in FIG. 1, transfection efficiency of MPG was not affected by bafilomycin A or cytochalasin B, suggesting that the cellular uptake of MPG/DNA complexes is independent of the classical endosomal pathway. In contrast, efficiency of the lipid-based carrier was dramatically reduced by these inhibitors of the endosomal pathway. Chloroquine barely increased the efficiency of MPG (only by 10%), whereas it enhanced delivery by Lipofectamine™ more than 20-fold, as already reported for different liposomal-based gene delivery systems (23, 24). When transfection experiments were performed at 4° C., the efficiency of MPG was reduced 12-fold, compared to that of Lipofectamine™ by more than 1000-fold. Based on these results, we believe that the decrease in the efficiency of MPG is associated with cellular stress induced by low temperature. To exclude the possibility that the MPG/DNA complexes remain associated with the cell membrane in the presence of inhibitors and only enter the cell upon dilution of the inhibitor, transfection experiments were performed in the presence of inhibitors, using a fluorescently labelled oligonucleotide (17). As reported in FIG. 1B, after one hour, most of the fluorescently labelled oligonucleotides localized to the nucleus and to cytoplasm of the cells, suggesting that MPG/DNA complexes are not associated with the membrane and indeed enter the cells in the presence of inhibitors. Interestingly, a small fraction of these complexes are associated with the membrane; may correspond to large aggregates unable to enter the cells. Taken together, these data suggest that the cellular uptake mechanism of MPG/DNA complexes is essentially independent of the endosomal pathway.

EXAMPLE 4

Role of the NLS of MPG in Nuclear Targeting of Plasmids

1. Material and Methods
Protein Preparation:
Plasmids for the expression of recombinant GST-fusion protein importin α and importin β were kindly provided by B. Cullen. Proteins were purified as described previously (13). For affinity chromatography experiments, protein GST-importin α and importin-β were coupled onto GST-bead in 150 mM NaCl, 1 mM EDTA and 10 mM Hepes pH 7.5. Importin-coupled beads were then incubated in batch with MPG/DNA complexes for 1 hr, extensively washed and incubated with 50 nM glutathione to elute the complexes. DNA was then extracted from the complexes with phenol-chloroform, followed by ethanol precipitation, and finally analyzed by agarose gel electrophoresis (0.8%).

2. Results

Figure 2:
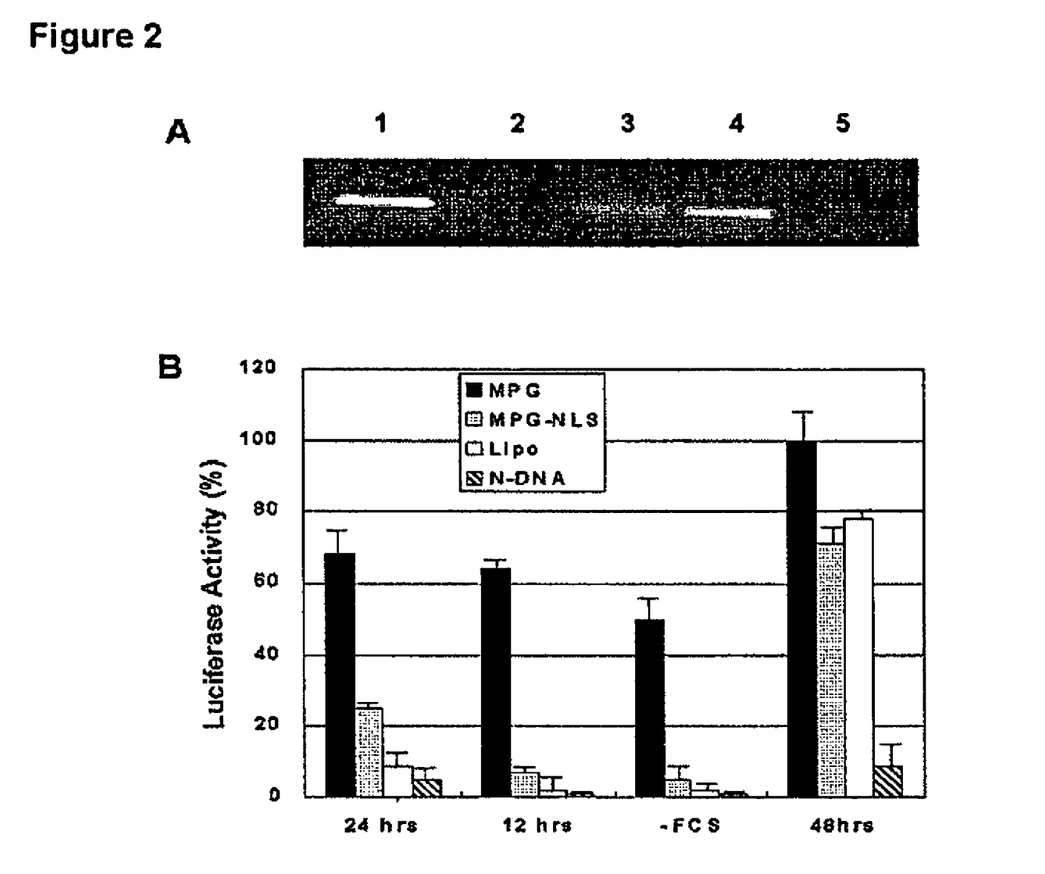

MPG peptide is derived from the nuclear localization sequence of the SV 40 large T antigen and from the fusion peptide domain of HIV-1 gp41 protein (17). Lysine residues are required for the formation of stable non-covalent interactions with DNA was demonstrated. To what extent the NLS sequence was involved in nuclear targeting of plasmids was investigated. Nuclear import of proteins is generally mediated by the interaction of the NLS with importin, which in turn favours the interaction with importin β (25, 26). Two peptides, wild-type MPG (SEQ ID NO:2) and MPG$^{\Delta NLS}$ (SEQ IDO:3), a variant characterized by a single mutation of the second lysine residue in the NLS motif to serine (KSKRKV) were used. This mutation has previously been reported to reduce import of NLS-containing proteins into the nucleus dramatically (25, 26). To determine to what extent the NLS moiety of MPG was required for nuclear import of plasmids, we first performed in vitro binding experiments using GST-fusion importin proteins. Importin α and 1 immobilized on beads were incubated with MPG/DNA or MPG$^{\Delta NLS}$/DNA complexes for 1 hr at 25° C. Then, both bound and unbound fractions were analyzed by agarose gel electrophoresis. As shown in FIG. 2A, MPG/DNA complexes significantly interacted specifically with importin α (lane 4) but not with importin β (lane 5). Moreover, binding of the complex to importin α was dramatically reduced when the plasmid was associated with MPG$^{\Delta NLS}$ (lane 3), suggesting that mutations in the NLS sequence significantly affect the interaction with importin α. As a control, it was verified that the plasmid alone did not interact with either importin α (lane 2) or β (data not shown).

One of the major limitations of most synthetic gene delivery systems, which significantly hampers gene delivery in vivo and into non-dividing cells is their poor ability to translocate plasmid DNA into the nucleus of cells (1). In order to study the impact of the NLS of MPG on nuclear translocation of plasmids, transfection experiments were performed on synchronized or growth-arrested cells with either MPG or its NLS mutant. Cells were synchronized in G0 by serum starvation then released back into the cell cycle by addition of serum. 4 hours after release, cells were transfected with MPG/DNA or MPG$^{\Delta NLS}$/DNA complexes and transgene expression was monitored 12 hours later, when most of the cells were in late G1, and 20 hours later, in late G2 prior to mitosis. Data were normalized with luciferase activity obtained 48 hours after transfection, and compared with asynchronous cells. As reported in FIG. 2B, high levels of luciferase expression were observed with MPG after only 12 hrs, which corresponds to 65% of expression observed after 48 hrs. After 24 hrs, transfection efficiency reached 70%. In contrast, when transfection was performed with MPG$^{\Delta NLS}$ (SEQ ID NO:3), luciferase activity was negligible after 12 hrs (7%), and only reached 26% after 24 hrs. Nevertheless, after 48 hrs, the efficiency of MPG$^{\Delta NLS}$ (SEQ ID NO:3) was 72% that of MPG. In comparison, lipid-based systems induced basal levels of luciferase activity after 12 hrs (10%), which may be explained by a fraction of unsynchronized, mitotic cells in the initial population. Similar experiments were performed on serum-starved, arrested cells, and transgene expression monitored 24 hrs after transfection revealed that when transfected with MPG, these cells exhibited 50% luciferase activity in comparison with dividing cells (FIG. 2B). In contrast no transfection was observed with either MPG$^{\Delta NLS}$ or lipid-based formulations. These data demonstrate that MPG facilitates translocation of DNA into the nucleus of arrested cells and that the NLS sequence plays a crucial role in its nuclear uptake. The low efficiency of transgene expression observed with MPG$^{\Delta NLS}$ reveals that nuclear translocation of MPG/DNA particles is directly mediated by the import machinery through interaction with importin α.

It must however be noted that MPG$^{\Delta NLS}$ is efficient for the transport of small size DNA.

EXAMPLE 5

Role of the Cysteamide Group in the Mechanism of MPG-Mediated Gene Delivery

Cysteamide was originally attached to the C-terminus of MPG, so as to enable covalent attachment of probes or drugs. We previously demonstrated that this modification did not affect the ability of MPG to form stable complexes with DNA. In order to investigate the impact of this C-terminal cysteamide group on gene delivery, comparative experiments were performed with an MPG peptide lacking a C-terminal cysteamide group. As shown in FIG. 1A (grey bars), luciferase expression levels measured following delivery of pRL-SV40 by MPG lacking a cysteamide group were 1000-fold lower than those observed with MPG modified with a cysteamide group. These data suggest that the cysteamide moiety is required to promote efficient transfection. One explanation for this observation is that the cysteamide stabilizes the carrier/DNA particle, as similarly reported for gene delivery mediated by cysteine-containing peptides (27).

EXAMPLE 6

MPG-Mediated Cyclin-B1 siRNA Delivery

1. Material and Methods

Cell culture, MPG mediated transfection. Adherent fibroblastic Hs68 (ATCC n° CRL-1635), 293 (ATCC n°CRL-1573), HeLa (ATCC n°CCL-2) and MCF-7 (ATCC n°HTB-22) cell lines were cultured in Dulbecco's Modified Eagle's Medium supplemented with 2 mM glutamine, 1% antibiotics (streptomycin 10'000 µg/ml, penicillin, 10'000 IU/ml) and 10% (w/v) fetal calf serum (FCS), at 37° C. in a humidified atmosphere containing 5% $CO_2$. For MPG-mediated delivery of siRNA, complexes were formed by incubation of different concentrations of siRNA from 10 nM to 1 µM with MPG at a molecular ratio of 1:10, respectively, in 500 µl of DMEM for 30 min at 37° C. Cells grown to 40 to 60% confluence were then overlaid with preformed complexes. After 30 min incubation at 37° C., 1 ml of fresh DMEM supplemented with 10% fetal calf serum was added directly to the cells, without removing the overlay of siRNA/MPG complexes, and cells were returned to the incubator. Different concentrations of siRNA or phosphorothioate oligonucleotide were transfected with cationic lipids, Lipofectamine or Oligofectamine (Invitrogen, Carlsbad, US), according to the guidelines of the manufacturer.

MPG-Mediated siRNA Delivery

```
siRNA targeting cyclin B1 were obtained from
Proligo/
                                            (SEQ ID NO:8)
Si-Cyclin B1 sense 5'GGCGAAGAUCAACAUGGCATT3', (SEQ ID NO:9)
Si-Cyclin B1 antisense 5'UGCCAUGUUGAUCUUCGCCTT3'

(SEQ ID NO:10)
Mismatch sense 5'GGUGAAGAUCAGCAUGGCATT3', (SEQ ID NO:11)
Mismatch antisense 5'UGCCAUGUCGAUCUUCACCTT3'
```

Cyclin B1 protein levels was determined by Western blotting: Hs68 or HeLa cells ($5\times10^6$ cells) were incubated with MPG/siRNA complexes. 30 hrs later, cells were collected and Protein were separated on SDS gel (12%), then transferred onto nitro-cellulose for Western blotting. Mouse monoclonal anti-cyclin B1 antibodies (SC-245) and rabbit polyclonal anti-Cdk2 antibodies (SC-163) for Western blotting were obtained from Santa Cruz Biotechnology Inc., (Santa Cruz, Calif.).

Cyclin B1 mRNA level was analyzed by Northern blotting. Hs68 or HeLa cells ($5 \times 10^6$ cells) were incubated with MPG/siRNA complexes. 15 hrs later, cells were collected and total RNA was isolated from cells with TriReagent™ (Sigma, Saint Louis) according to the manufacturer's instructions. RNA was then purified by phenol extraction followed by ethanol precipitation. RNA samples (10 µg) were separated by electrophoresis on formaldehyde agarose gels (1.2%), transferred to a nylon membrane (Hybond N+, Amersham Pharmacia Biotech) and hybridized with $^{32}$P-radiolabelled probes corresponding to the full-length cDNA of cyclin B1 or of GAPDH, respectively, prepared by random priming using the High Prime DNA labeling kit (Roche Diagnostics). Following hybridization and washing, the membrane was exposed to a Phosphorimaging screen and signals were acquired on a Phosphorimager (Molecular Dynamics).

Cyclin B1 siRNA inhibits tumor growth: In vivo injections and tumors analysis. Five weeks old female Swiss nude nice were injected subcutaneously with $2 \times 10^7$ 15PC3 cells or A549 cells (n° ATCC CCL-185) (human bronchoalveolar carcinoma). When tumors reached a mean volume of 50 to 100 nm$^3$, (a week later), mice were injected intra-tumorally or sub-tumorally with 501 µl of PBS containing anti cyclin B1 siRNA (1, 5, 10 µg) or scrambled siRNA (50 µg) complexed with MPG or siRNA (50 µg). 50 µl of PBS was used as a control. Tumor volume was measured with calipers every two days. A second injection was performed after 10 days and tumor size was measured after 20 days.

2. Results siRNA cyclin B1 promotes robust down-regulation of cyclin B1 Increasing concentrations (lane 3: 10 nM, lane 4: 25 nM, lane 5: 50 nM, lane 6: 100 nM, lane 7: 150 nM) of siRNA (FIG. 5) were incubated with MPG at a molar ratio 1:10 at 37° C. for one hour, then overlaid onto cultured cells. Cyclin B1 protein was analyzed by Western blotting after 30 hrs. Cdk2 protein was used as a control to normalize protein levels. Cyclin B1 mRNA was analyzed by Northern blotting after 12 hrs. GAPDH was used as a control to normalize mRNA levels.

Cell cycle progression is driven by sequential activation of essential heterodimeric protein kinase complexes (Cdk/cyclin complexes). Most of the drugs currently designed to target cell cycle progression are directed against the kinase activity of the Cdk subunits. However, as such drugs generally tend to affect other cellular kinases non specifically, we have recently proposed to target the regulatory cyclin subunit instead, as a more appropriate means of improving both the selectivity and the efficiency of cell cycle inhibitors. Cyclin B1 in particular constitutes a key target for cancer therapy, as a component of the essential "Mitosis Promoting Factor" together with protein kinase Cdk1. It is shown that MPG-mediated delivery of siRNA targeting cyclin B1 yielded a robust biological response.

Figure 5:
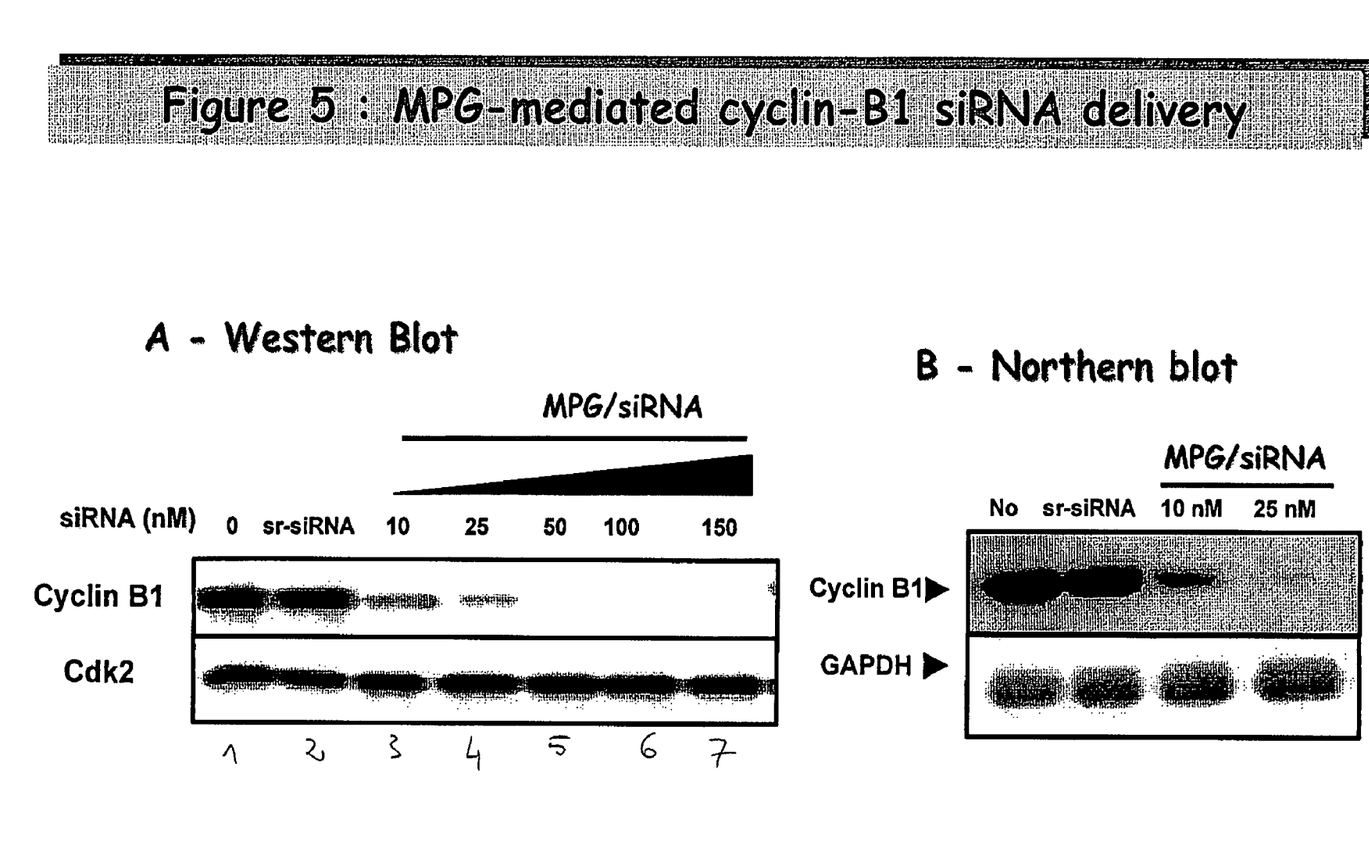
FIG. 5: MPG-mediated cyclin-B1 siRNA delivery. A/Western blot: Increasing concentrations (lane 3: 10 nM, lane 4: 25 nM, lane 5: 50 nM, lane 6: 100 nM, lane 7: 150 nM) of siRNA were incubated with MPG at a molar ratio 1:10 at 37° C. for one hour, then overlaid onto cultured cells. Cyclin B1 protein was analyzed by Western blotting after 30 hrs. Cdk2 protein was used as a control to normalize protein levels. B/Northern blot: Cyclin B1 mRNA was analyzed by Northern blotting after 12 hrs. GAPDH was used as a control to normalize mRNA levels.

* It was firstly shown that cyclin B1 protein levels were down-regulated by MPG-mediated delivery of siRNA, and to what extent, compared to delivery of siRNA and classical antisense oligonucleotide using lipid formulation. The effect of increasing concentrations of siRNA from 10 nM to 200 nM complexed with MPG (ratio 1:10) or with classical cationic lipids on cyclin B1 protein levels was analyzed in several cell lines, including Hela cells, human fibroblasts (Hs68) and 293 cells (FIG. 5). SiRNA/MPG complexes were overlaid onto asynchronous cultured cells in the presence of FBS (10%), and cyclin B1 protein levels were quantified by Western blotting 30 hrs after transduction. Cdk2 protein kinase was used as a control to normalize protein levels. Similar results were obtained for the three cell lines and typical Western blots for Hs68 fibroblasts are shown in the figure. Cyclin B1 protein levels were significantly reduced with 10 nM siRNA and completely abolished with 50 nM siRNA complexed with MPG. In contrast, cyclin B1 protein levels were not affected by either 2 µM scrambled or mismatched siRNA/MPG complexes or free siRNA.

Figure 6:
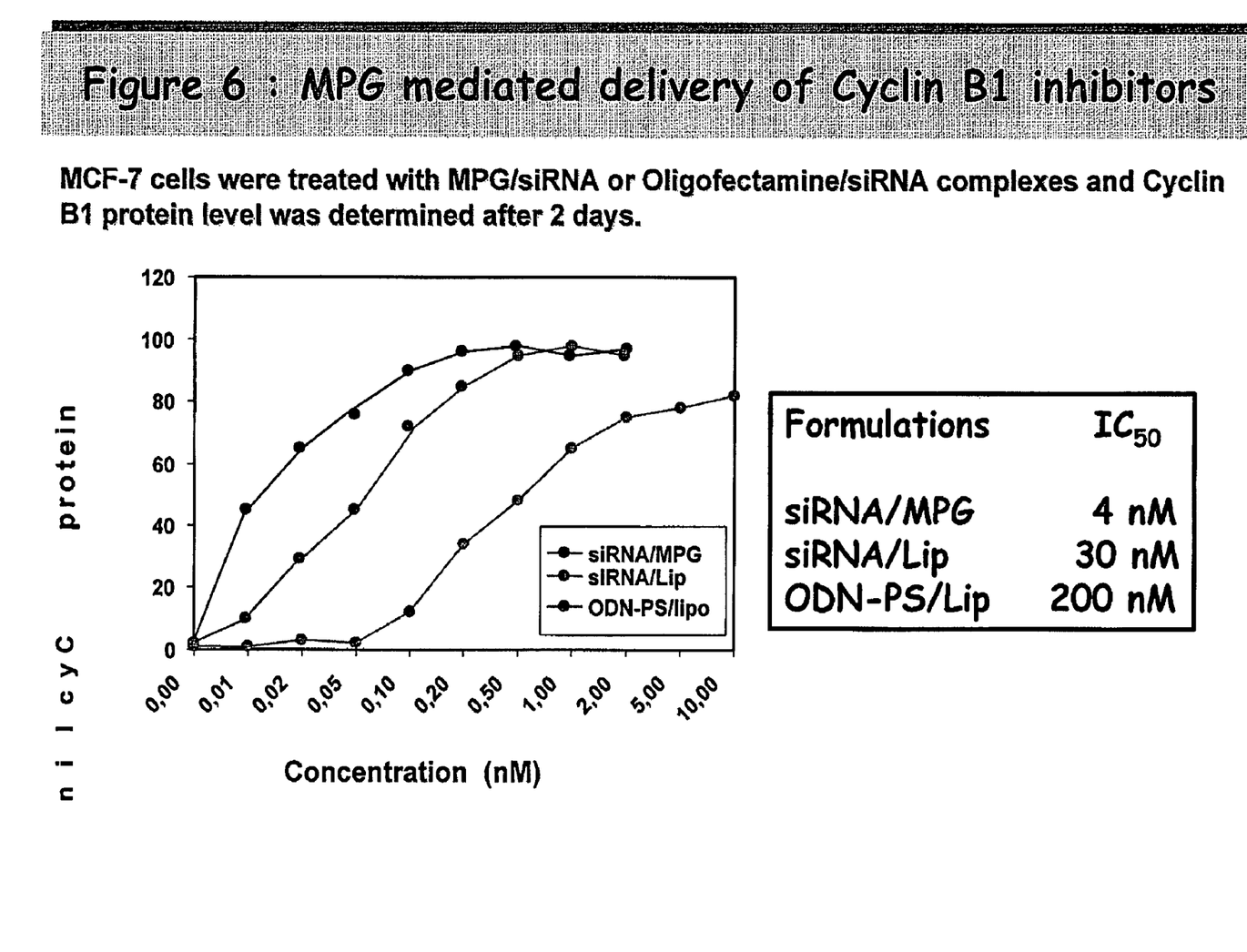
FIG. 6: MPG mediated delivery of cyclin B1 inhibitors. Comparative anti-sense effects of the different strategies aimed at targeting cyclin B were estimated using ImageQuant to quantify cyclin B levels acquired from Western blots. The values represent the average of three separate experiments. MPG/siRNA, siRNA delivered with cationic lipids and PS-oligonucleotide delivered with cationic lipids. MCF7 cells were treated with MPG/siRNA or oligofectamine/siRNA complexes and cyclin protein level was determined after 2 days.

MPG mediated delivery of cyclin B1 inhibitors. Comparative anti-sense effects of the different strategies aimed at targeting cyclin B were estimated using ImageQuant to quantify cyclin B levels acquired from Western blots (FIG. 6). The values represent the average of three separate experiments. MPG/siRNA, siRNA delivered with cationic lipids and PS-oligonucleotide delivered with cationic lipids.

Quantification of cyclin B protein levels from these Western blots allowed to estimate IC$_{50}$ values for downregulation of cyclin B1, and thereby to compare the potency of MPG/siRNA complexes with that of the other antisense strategies targeting Cyclin B1 or siRNA delivery methods (FIG. 4). SiRNA/MPG complexes have a potent silencing effect with an IC$_{50}$ of $4\pm0.1$ nM, value which is 8.5-fold and 50-fold lower than that of cationic lipid-mediated delivery of siRNA (IC$_{50}$: $30\pm2$ nM) and of classical phosphorothioate-oligonucleotide (IC$_{50}$: $200\pm12$ nM), respectively. Taken together, these results demonstrate that MPG constitutes a much more appropriate system for delivery of siRNA.

Antisense Cyclin B1 HypNA-PNA Inhibits Proliferation of Cancer Cells

Figure 7:
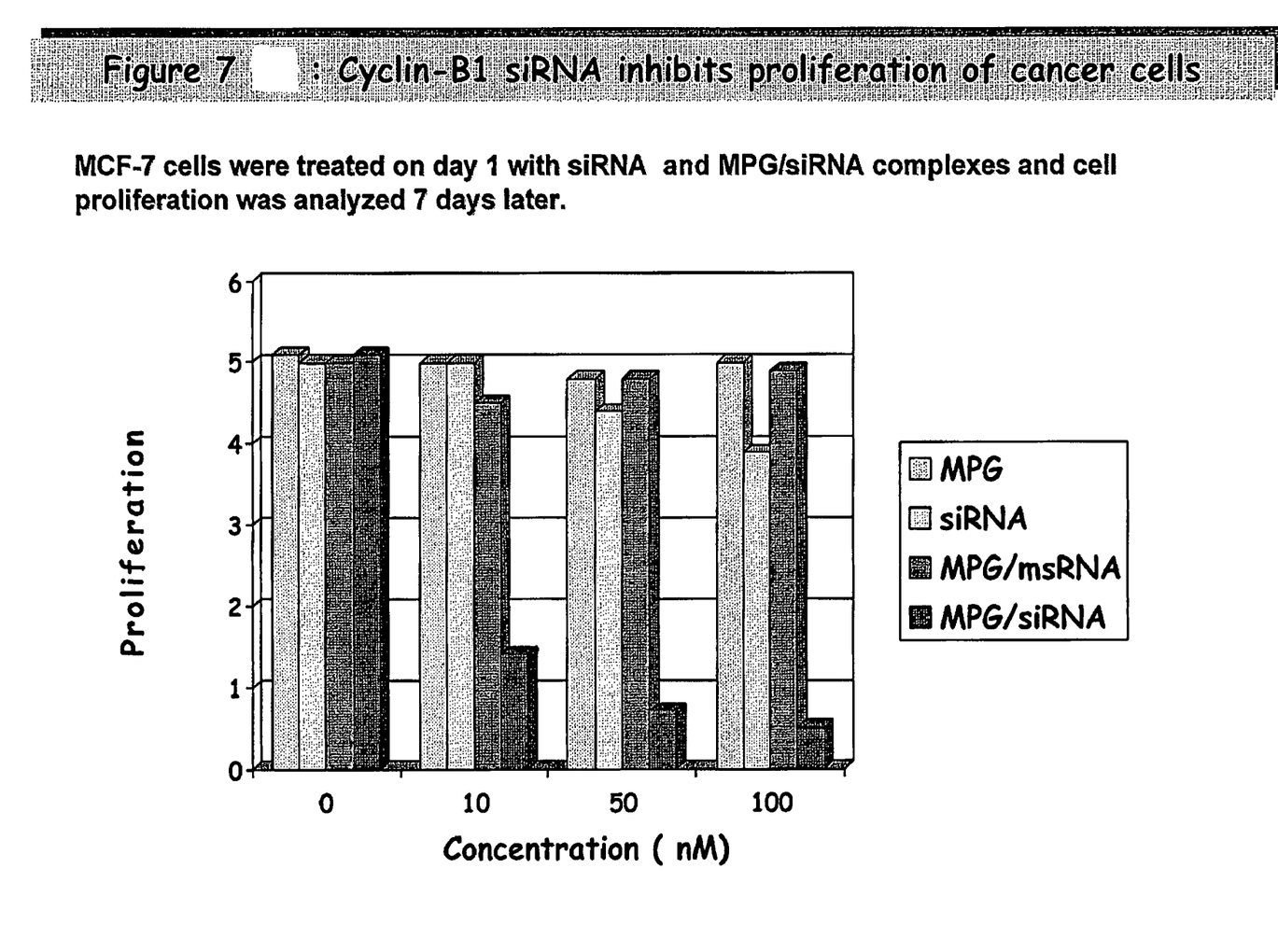
FIG. 7: Cyclin-B1 siRNA inhibits tumour growth. Exponentially MCF-7 growing cells (1-3 $10^4$) were incubated with different concentrations (10 nM, 50 nM, 100 nM) of siRNA or mismatched siRNA complexed or not with MPG (molecular ratio 1:10) and cell proliferation was assessed 8 days post incubation.

As delivery of siRNA directed against cyclin B1 promotes efficient downregulation of both cyclin B1 mRNA and protein levels, it was looked for to what extent this might affect proliferation of cancer cells. The effect of siRNA was investigated on the human breast cancer cell line MCF-7. Exponentially growing cells (1-3 10$^4$) were incubated with different concentrations (10 nM, 50 nM, 100 nM) of siRNA or mismatched siRNA complexed or not with MPG (molecular ratio 1:10) and cell proliferation was assessed 8 days post incubation (FIG. 7). Concentrations of 10 nM and 50 nM of siRNA consistently reduced cell proliferation by 70% and 95%, respectively. In comparison, neither free siRNA or scrambled molecules, or the peptide carrier alone affected cell proliferation, except for the highest concentrations of free siRNA, which exhibited a slight decrease in cell proliferation. Notwithstanding, these results emphasize the essential role of MPG in improving the bio-availability of siRNA molecules.

Figure 8:
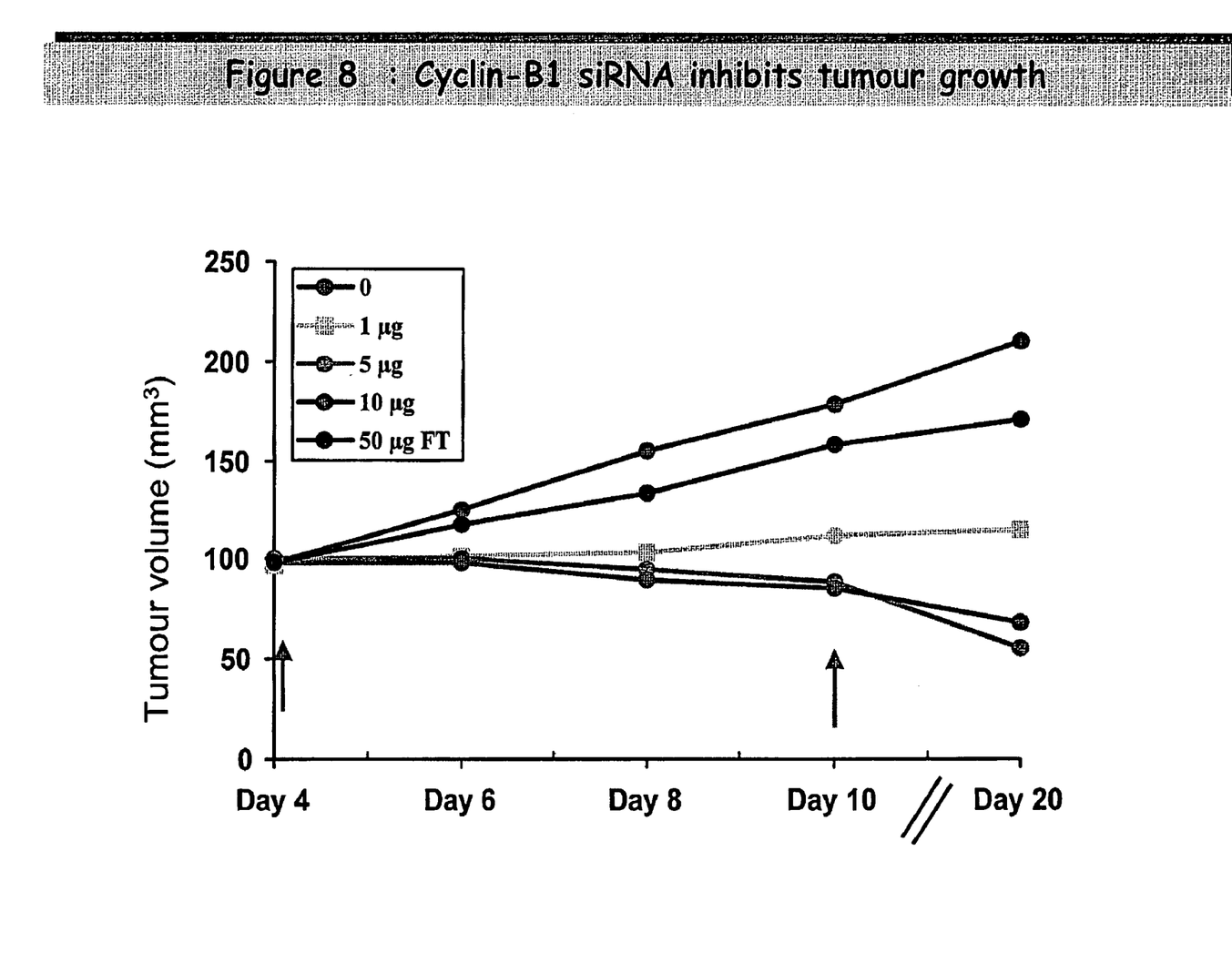
FIG. 8: Cyclin-B1 siRNA inhibits tumour growth. Mice were infected subcutaneously with 15PC3 cells (ATCC n°CRL-1435). One week later, MPG/siRNA complexes were injected directly into the tumour, at different concentrations (1 µg, 5 µg, 10 µg, in 50 µl of PBS).

As delivery of siRNA directed against cyclin B1 blocked proliferation of cancer cells, the role of siRNA/MPG formulation to block tumor growth in vivo. The effect of the cyclin B1 siRNA was investigated on tumor animal model (FIG. 8), using Swiss nude nice, injected subcutaneously with $2 \times 10^7$ 15PC3 cells or A549 cells (human bronchoalveolar carcinoma). Different MPG/siRNA complexed were injected intra-tumorally and monitoring tumor volumes followed the effect of siRNA. In a control experiment, we demonstrated than 20 days after injection of PBS or MPG alone, the tumor size increased by 2.5 fold. In contrast, no growth of the tumor is observed, when injected with MPG/siRNA even with low concentration of siRNA. These results suggested than siRNA specifically inhibits tumor growth and thanks to the used of MPG as carrier only low concentration of siRNA are required for a marked anti-tumoral effect. Moreover, a significant reduction in the tumor size after a second injection of MPG/siRNA was observed. These results show that MPG constitutes an excellent tool for in vivo delivery of siRNA. These results constitute the first in vivo therapeutic application of a carrier system/siRNA complex.

EXAMPLE 7

Implication of the NLS Sequence of MPG in the Kinetics of the Response to siRNA To further understand the impact of the NLS in MPG, we examined the biological response of an siRNA targeting the GAPDH gene following transfection into human fibroblasts (Hs68). Data found with Hs68 human fibroblasts were essentially the same with Hela and Cos 7 cells (data not shown). Different concentrations of siRNA (25, 50, 100 nM) were transfected with either MPG or MPG$^{\Delta NLS}$ and the levels of GAPDH protein were analyzed by Western blotting 30 hrs post transfection. As shown in FIG. 4B, GAPDH protein levels were dramatically reduced when siRNA were transfected with either MPG carrier. Quantification of the signals revealed that a concentration of 25 nM siRNA transfected with MPG$^{\Delta NLS}$ reduced GAPDH protein levels by 80%, whereas 100 nM siRNA was required to reduce GAPDH levels by 60% when delivered by wild-type MPG, demonstrating that MPG$^{\Delta NLS}$ is at least 2-fold more efficient. The kinetics of siRNA-induced degradation of GAPDH mRNA following transfection with either MPG or MPG$^{\Delta NLS}$ were analyzed by Northern blotting. As shown in FIG. 4C, MPG promoted a significant reduction of GAPDH mRNA after 20 hrs, which was initiated after 10 hrs. In comparison, MPG$^{\Delta NLS}$ induced a robust downregulation of GAPDH mRNA after 5 hrs only. These data are comparable to those already reported for lipid-mediated siRNA delivery and suggest that the rapid release of siRNA into the cytoplasm significantly improves the silencing response. Taken together, this set of experiments has lead us to conclude that mutations which affect the NLS of MPG are essential to design a potent vector for specific delivery of siRNA.

REFERENCES

1. Luo, D. & Saltzman, M. (2000) Synthetic DNA delivery systems. *Nat. Biotechnol.* 18, 33-37.
2. Mahato, R. I. (1997) Non-viral peptide-based approaches to gene delivery. *J Drug Target.* 7, 249-68
3. Morris, M. C., Chaloin, L., Heitz, F. & Divita, G. (2000) Translocating peptides and proteins and their use for gene delivery. *Curr. Opin. Biotechnol.* 11, 461-466
4. Gariepy, J. & Kawamura, K. (2000) Vectorial delivery of macromolecules into cells using peptide-based vehicles. *Trends Biotechnol.,* 19, 21-26
5. Wyman, T. B., Nicol, F., Zelphati, O., Scaria, P. V., Plank, C., & Szoka, F. C. Jr. (1997) Design, synthesis, and characterization of a cationic peptide that binds to nucleic acids and permeabilizes bilayers. *Biochemistry* 36, 3008-3017
6. Gottschalk, S., Sparrow, J. T., Hauer, J., Mims, M. P., Leland, F. E., Woo, S. L., & Smith, L. C. (1996) A novel DNA-peptide complex for efficient gene transfer and expression in mammalian cells. *Gene Ther.* 3, 48-57
7. Rittner, K., Benavente, A., Bompart-Sorlet, A., Heitz, F., Divita, G., Brasseur, R., & Jacob, E. (2002) New basic membrane-destabilizing peptides for plasmid-based gene delivery in vitro and in vivo. *Mol. Ther.* 5, 104-114.
8. Cartier, R., & Reszka, R. (2002) Utilization of synthetic peptides containing nuclear localization signals for nonviral gene transfer systems. *Gene Ther.* 9, 157-167
9. Morris, M. C., Chaloin, L., Heitz, F. & Divita, G. (2002) Signal sequence-based cell-penetrating peptides and their applications for gene delivery. Cell Penetrating peptides: Processes and application, Editor U. Langel, CRC press, Pharmacology & Toxicology series.
10. Lindgren, M., Hällbrink, M., Prochiantz, A. & Langel, U. (2000) Cell-penetrating peptides. *Trend Pharmacol. Sci.* 21, 99-103.
11. Wadia, J. S. & Dowdy, S. F. (2002) Protein transduction technology. *Curr Opin Biotechnol* 13, 52-56
12. Dom, G., Shaw-Jackson, C., Matis, C., Bouffioux, O., Picard, J. J., Prochiantz, A., Mingeot-Leclercq, M. P., Brasseur, R., & Rezsohazy, R. (2003) Cellular uptake of Antennapedia Penetratin peptides is a two-step process in which phase transfer precedes a tryptophan-dependent translocation. *Nucleic Acids Res.* 31, 556-561
13. Truant, R. & Cullen, B. R. (1999) The arginine-rich domains present in human immunodeficiency virus type 1 Tat and Rev function as direct importin beta-dependent nuclear localization signals. Mol Cell Biol. 19, 1210-1207
14. Torchilin, V. P., Rammohan, R., Weissig, V., & Levchenko, T. (2001) TAT peptide on the surface of liposomes affords their efficient intracellular delivery even at low temperature and in the presence of metabolic inhibitors. *Proc Natl Acad Sci USA* 98, 8786-8791
15. Torchilin, V. P., Levchenko, T. S., Rammohan, R., Volodina, N., Papahadjopoulos-Sternberg, B., & D'Souza, G. G. (2003) Cell transfection in vitro and in vivo with non-toxic TAT peptide-liposome-DNA complexes. *Proc Natl Acad Sci USA* 100, 1972-1977
16. Rudolph, C., Plank, C., Lausier, J., Schillinger, U., Muller, R. H., & Rosenecker, J. (2003) Oligomers of the arginine-rich motif of the HIV-1 TAT protein are capable of transferring plasmid DNA into cells. *J Biol. Chem.* 278, 11411-11418.
17. Morris, M. C., Vidal, P., Chaloin, L., Heitz, F, & Divita G. (1997) A new peptide vector for efficient delivery of oligonucleotides into mammalian cells. *Nucleic Acids Res.* 25, 2730-2736
18. Morris, M. C., Chaloin, L., Mery, J., Heitz, F., & Divita G. (1999) A novel potent strategy for gene delivery using a single peptide vector as a carrier. *Nucleic Acids Res.* 27, 3510-3517
19. Vidal, P., Morris, M. C, Chaloin, L., Heitz, F. & Divita G. (1997) New strategy for RNA vectorization in mammalian cells. Use of a peptide vector. *C R Acad Sci III* 320, 279-287
20. Silverstein, S. C., Steinman, R. M., & Cohn, Z. A. (1977) Endocytosis. *Annu. Rev. Biochem.* 46, 669-710.
21. Bowman, E. J., Siebers, A., & Altendorf, K. (1988) Bafilomycins: A class of inhibitors of membrane ATPases from microorganisms, animal cells and plant cells. *Proc. Natl. Acad. Sci. USA.,* 85, 7972-7980
22. Maxfield, F. R. (1982) Weak bases and ionophores rapidly and reversibly raise the pH of endocytic vesicles in cultured mouse fibroblasts. *J. Cell Biol.,* 95, 676-682
23. Brisson, M., Tseng, W. C., Almonte, C., Watkins, S., & Huang, L. (1999) Subcellular trafficking of the cytoplasmic expression system. *Hum. Gene Ther.* 10, 2601-2611.
24. Zelphati, O., & Szoka, F. C. Jr. (1996) Mechanism of oligonucleotide releases from cationic liposomes. *Proc Natl Acad Sci USA* 93, 11493-11498
25. Mattaj, I. W., & Englmeier, L. (1998) Nucleocytoplasmic transport: the soluble phase. *Annu. Rev. Biochem.* 67, 265-306
26. Cullen, B. R. (2001) Journey to the center of the cell. *Cell,* 105, 697-700
27. McKenzie, D. L., Kwok, K. Y., & Rice, K. G. (2000) A potent new class of reductively activated peptide gene delivery agents. *J. Biol. Chem.* 275, 9970-9977.

28. Elbashir, S. M., Harborth, J., Lendeckel, W., Yalcin, A., Weber, K., & Tuschl, T. (2001) Duplexes of 21-nucleotide RNAs mediate RNA interference in cultured mammalian cells. *Nature* 411, 494-498.
29. Hannon, G. J. (2002) RNA interference. *Nature* 418, 244-251
30. Richard, J. P., Melikov, K., Vives, E., Ramos, C., Verbeure, B., Gait, M. J., Chernomordik, L. V., & Lebleu, B. (2003) Cell-penetrating peptides. A reevaluation of the mechanism of cellular uptake. *J Biol. Chem.* 278, 585-590.
31 Pichon, C., Monsigny, M., & Roche, A. C. (1999) Intracellular localization of oligonucleotides: influence of fixative protocols. *Antisense Nucleic Acid Drug Dev* 9, 89-93.
32. Koppelhus, U., Awasthi, S. K., Zachar, V., Holst, H. U., Ebbesen. P., & Nielsen. P. E. (2002) Cell-dependent differential cellular uptake of PNA, peptides, and PNA-peptide conjugates. *Antisense Nucleic Acid Drug Dev* 2, 51-63
33. Langel, U. (2002) Cell Penetrating Peptides: Processes and Applications, CRC press, Pharmacology & Toxicology series
34. Zanta, M. A., Belguise-Valladier, P., & Behr, J. P. (1999) Gene delivery: A single nuclear localization signal peptide is sufficient to carry DNA to the cell nucleus. *Proc. Natl. Acad. Sci. USA*, 96, 91-94.
35. Ciolina, C., Byk, G., Blanche, F., Thuillier, V., Scherman, D., & Wils, P. (1999) Coupling of nuclear localization signals to plasmid DNA and specific interaction of the conjugates with importin. *Bioconjug. Chem.*, 10, 49-54.
36. Branden, L. J., Mohamed, A. J., & Smith, C. I. (1999) A peptide nucleic acid-nuclear localization signal fusion that mediates nuclear transport of DNA. *Nat Biotechnol.* 17, 784-787.
37. Subramanian, A., Ranganathan, P., Diamond, S. L. (1999) Nuclear targeting peptide scaffolds for lipofection of non-dividing mammalian cells. *Nat. Biotechnol.* 17, 873-877
38. Zeng, Y., & Cullen, B. R. (2002) RNA interference in human cells is restricted to the cytoplasm. *RNA* 8, 855-860
39. Mery J. et al., Int. J. Peptide Protein Res., 1993, 42, 44-52.

The invention claimed is:

1. A complex comprising a peptide carrier consisting of SEQ ID NO: 2 and an appropriate siRNA, wherein said siRNA is selected to silence a target mRNA.

2. The complex of claim 1, wherein the peptide carrier and the siRNA are present in a molar ratio of from about 1:1 to about 20:1

3. The complex of claim 1, wherein the peptide carrier and the siRNA are present in a molar ratio of about 10:1.

4. A peptide carrier comprising SEQ ID NO: 2.

5. A peptide carrier consisting of SEQ ID NO: 2.

6. A composition comprising the complex of claim 1 and a suitable vehicle.

7. A transfection kit comprising at least one appropriate buffer, positive and negative controls and at least one complex as defined in claim 1, wherein the complex is either in solution or has been lyophilized.

* * * * *